United States Patent
Phipps et al.

(10) Patent No.: US 7,303,348 B2
(45) Date of Patent: Dec. 4, 2007

(54) DOSING DISPENSER FOR CREAM-BASED MEDICINES

(75) Inventors: Timothy Phipps, Woodstock, GA (US); Dale Coker, Acworth, GA (US); Carter Gorman, Suwanee, GA (US); Lindsey Pickle, Marietta, GA (US); Matthew Poelke, Marietta, GA (US); Larry Wilson, Acworth, GA (US); Donald Anthony Muntner, Loganville, GA (US)

(73) Assignee: Custom Rx Tda, LLC, Woodstock, GA (US)

( * ) Notice: Subject to any disclaimer, the term of this patent is extended or adjusted under 35 U.S.C. 154(b) by 0 days.

(21) Appl. No.: 11/745,228

(22) Filed: May 7, 2007

(65) Prior Publication Data

US 2007/0206987 A1    Sep. 6, 2007

Related U.S. Application Data

(63) Continuation of application No. 11/428,470, filed on Jul. 3, 2006, now Pat. No. 7,213,994.

(60) Provisional application No. 60/695,962, filed on Jul. 1, 2005.

(51) Int. Cl.
*B43K 5/06* (2006.01)
*B43K 21/08* (2006.01)

(52) U.S. Cl. ............... 401/175; 401/75; 401/172; 222/390; 222/391

(58) Field of Classification Search ............ 401/64–68, 401/74, 75, 82–84, 172, 175, 176, 179, 262, 401/277; 222/390, 391
See application file for complete search history.

(56) References Cited

U.S. PATENT DOCUMENTS

| | | | |
|---|---|---|---|
| 3,007,611 | A | 11/1961 | Coolidge |
| 3,333,740 | A | 8/1967 | Waller |
| 3,616,970 | A | 11/1971 | Baumann et al. |
| 3,873,008 | A | 3/1975 | Jahn |
| 4,074,833 | A | 2/1978 | Otto, Sr. |
| 4,139,127 | A | 2/1979 | Gentile |
| 4,298,036 | A | 11/1981 | Horvath |
| 4,363,560 | A | 12/1982 | Gentile |
| 4,544,083 | A | 10/1985 | Schroeder |
| 4,641,776 | A | 2/1987 | Vlasek et al. |
| 4,658,993 | A | 4/1987 | Vlasich |
| 4,850,516 | A | 7/1989 | Seager |
| 4,865,231 | A | 9/1989 | Wiercinski |
| 5,000,356 | A | 3/1991 | Johnson et al. |
| 5,007,755 | A | 4/1991 | Thompson |
| 5,016,782 | A | 5/1991 | Pfanstiel |
| 5,025,960 | A | 6/1991 | Seager |
| 5,540,361 | A | 7/1996 | Fattori |
| 5,573,341 | A | 11/1996 | Iaia |
| 5,725,133 | A | 3/1998 | Iaia |

(Continued)

*Primary Examiner*—Tuan Nguyen
(74) *Attorney, Agent, or Firm*—Jason A. Bernstein; Powell Goldstein LLP

(57) ABSTRACT

A dispenser for metered dosing of cream-based medicines comprising a barrel, a base having a threaded rod extending therefrom, a riser having at least one flexible seal which engages the barrel, an applicator cap having apertures therein for spreading dispensed cream onto a user's skin. The user positively knows when a metered amount of cream has been dispensed by tactile and audible feedback.

1 Claim, 11 Drawing Sheets

U.S. PATENT DOCUMENTS

| | | |
|---|---|---|
| 5,839,622 A | 11/1998 | Bicknell et al. |
| 5,947,621 A | 9/1999 | Szekely |
| 6,039,483 A | 3/2000 | Szekely |
| 6,186,686 B1 | 2/2001 | Neuner et al. |
| 6,811,062 B2 | 11/2004 | Tani |
| 6,969,209 B2 | 11/2005 | Apar et al. |
| 7,213,994 B2 * | 5/2007 | Phipps et al. ............ 401/175 |
| 2003/0197028 A1 | 10/2003 | Jaekel |
| 2003/0197037 A1 | 10/2003 | Manganini |
| 2004/0069814 A1 | 4/2004 | Hemming et al. |
| 2004/0206783 A1 | 10/2004 | Danne et al. |
| 2005/0025558 A1 | 2/2005 | Severa |
| 2005/0178796 A1 | 8/2005 | Shraiber |

\* cited by examiner

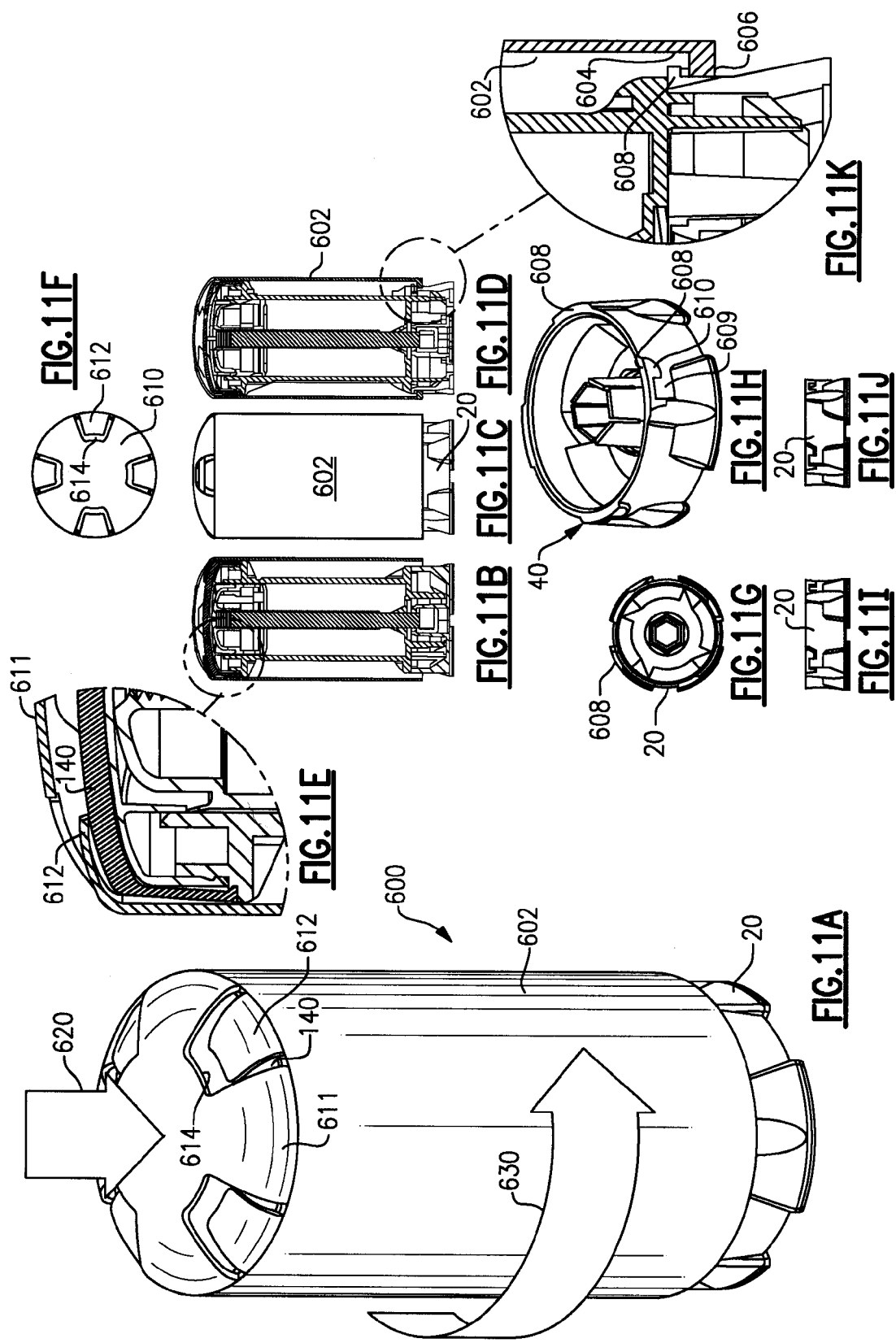

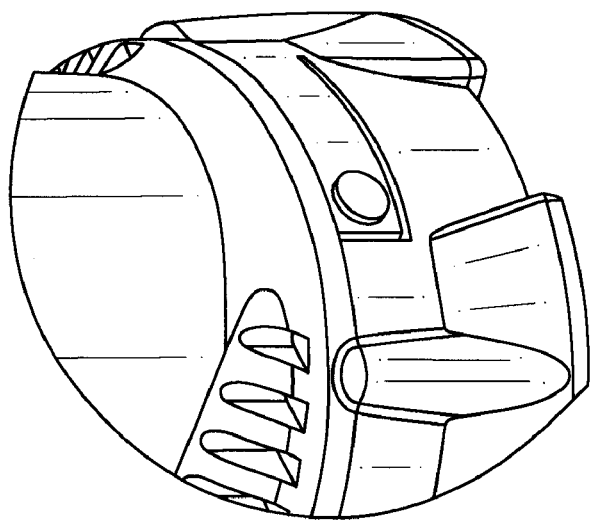
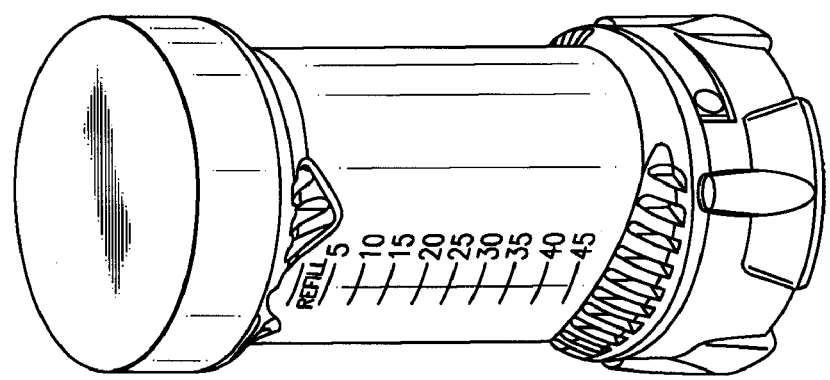
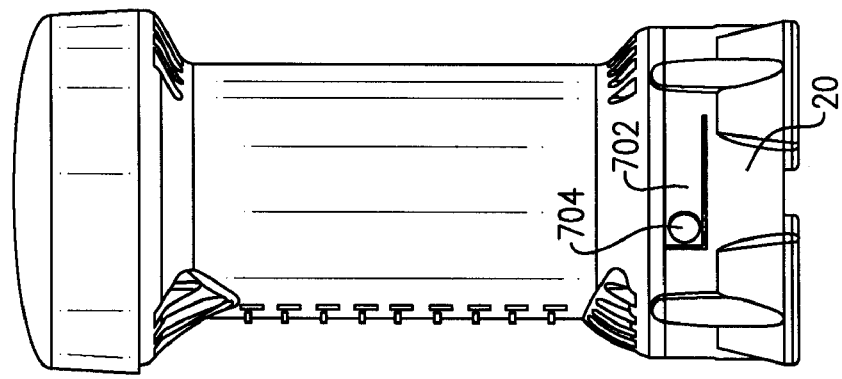
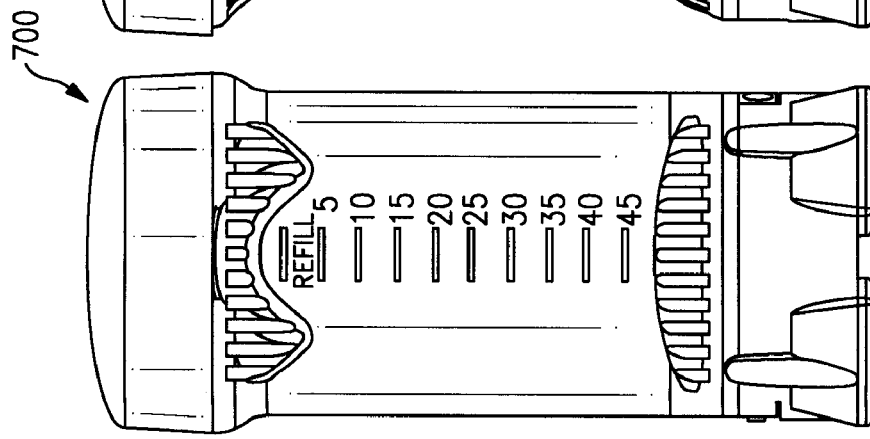

US 7,303,348 B2

DOSING DISPENSER FOR CREAM-BASED MEDICINES

CROSS-REFERENCE TO RELATED APPLICATIONS

This application is a continuation of U.S. patent application Ser. No. 11/428,470, filed Jul. 3, 2006, now U.S. Pat. No. 7,213,994, entitled DOSING DISPENSER FOR CREAM-BASED MEDICINES, which claims benefit of U.S. Provisional Patent Application No. 60/695,962, filed Jul. 1, 2005, entitled SYSTEMS AND METHODS FOR DISPENSING MEDICINE, the disclosures of which are incorporated by reference in their entirety.

FIELD OF THE INVENTION

The present invention relates to dispensers for cream-based medicines, and more particularly, to a dispenser having a rotatable housing which causes a floor member to rise and urge a predetermined amount of cream through an opening in a cap.

BACKGROUND OF THE INVENTION

Traditionally, topically administered medicine was often formulated as liquids. Applying a liquid to a skin surface often resulted in a portion of the dose spreading beyond the target area. Cream-based formulations were developed as viscous liquids to prevent the unintended application of the medicine to an unaffected area. More recently, pharmacists have been taking traditional medicines and "compounding" them in a cream base.

Administering the cream-based medicines is a challenge because providing an accurate measured dose is not easy. One common form of dispenser is a traditional hypodermic syringe, without the needle. The user can depress the plunger to force an amount of cream out of the barrel as indicated by markings on the side of the barrel. For older patients it is not always easy to measure out 0.1 ml or so of medicine as this may require more dexterity than available. It would be desirable to have a dispenser for cream-based medicines that is easier to use and which provides a positive confirmation that the desired amount of cream has been dispensed.

SUMMARY OF THE INVENTION

Generally described, the present invention provides several embodiments of a dispensing apparatus which utilizes a novel rotation mechanism. In one exemplary embodiment a dispenser includes a base having a threaded rod extending therefrom over which can be fitted a riser which advances when the base is turned. The riser and rod reside within a barrel. The barrel has an applicator cap through which the cream is forced and which provides a surface to apply the cream to the skin. The dispenser also preferably includes a cap to retard drying out of the cream and to protect the applicator cap from becoming contaminated. When used the base is turned and a positive audible and tactile click is sensed, indicating that a portion of cream has been dispensed. The base cannot be turned in the reverse direction, thereby effectively eliminating the possibility of cream being drawn back into the barrel.

The present invention also provides a means for filling the dispenser so as to reduce bubbles and pockets in the cream after being inserted into the barrel.

Accordingly, it is a feature of the present invention to provide a dispenser for the metered dosing of cream-based medicine in a manner that provides a positive sensory feedback mechanism to confirm that the desired amount of cream has been dispensed.

It is another feature of the present invention to provide a dosing dispenser that will allow the user to administer the cream evenly to the skin area.

Other features and advantages of the present invention will become apparent upon reading the following detailed description of embodiments of the invention, when taken in conjunction with the appended claims.

BRIEF DESCRIPTION OF THE DRAWINGS

The invention is illustrated in the drawings in which like reference characters designate the same or similar parts throughout the figures of which:

FIGS. 11A-K show an alternative embodiment incorporating a first design of a safety cap.

FIGS. 12A-D show an alternative embodiment incorporating a second design of a safety switch or mechanism.

DETAILED DESCRIPTION OF THE INVENTION

Figure 1:
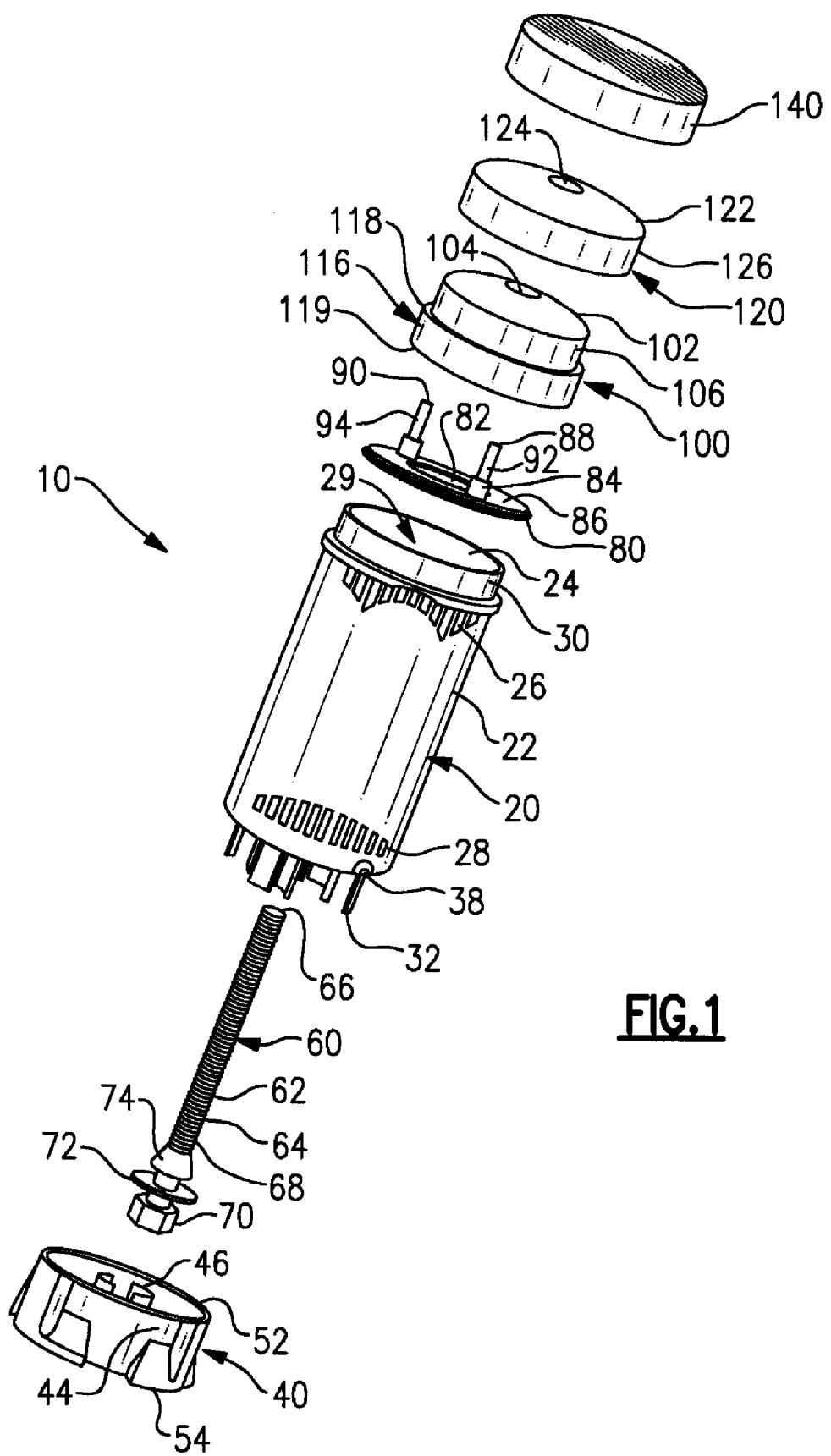
FIG. 1 is an exploded schematic view of one exemplary embodiment of the present invention.
Figure 2:
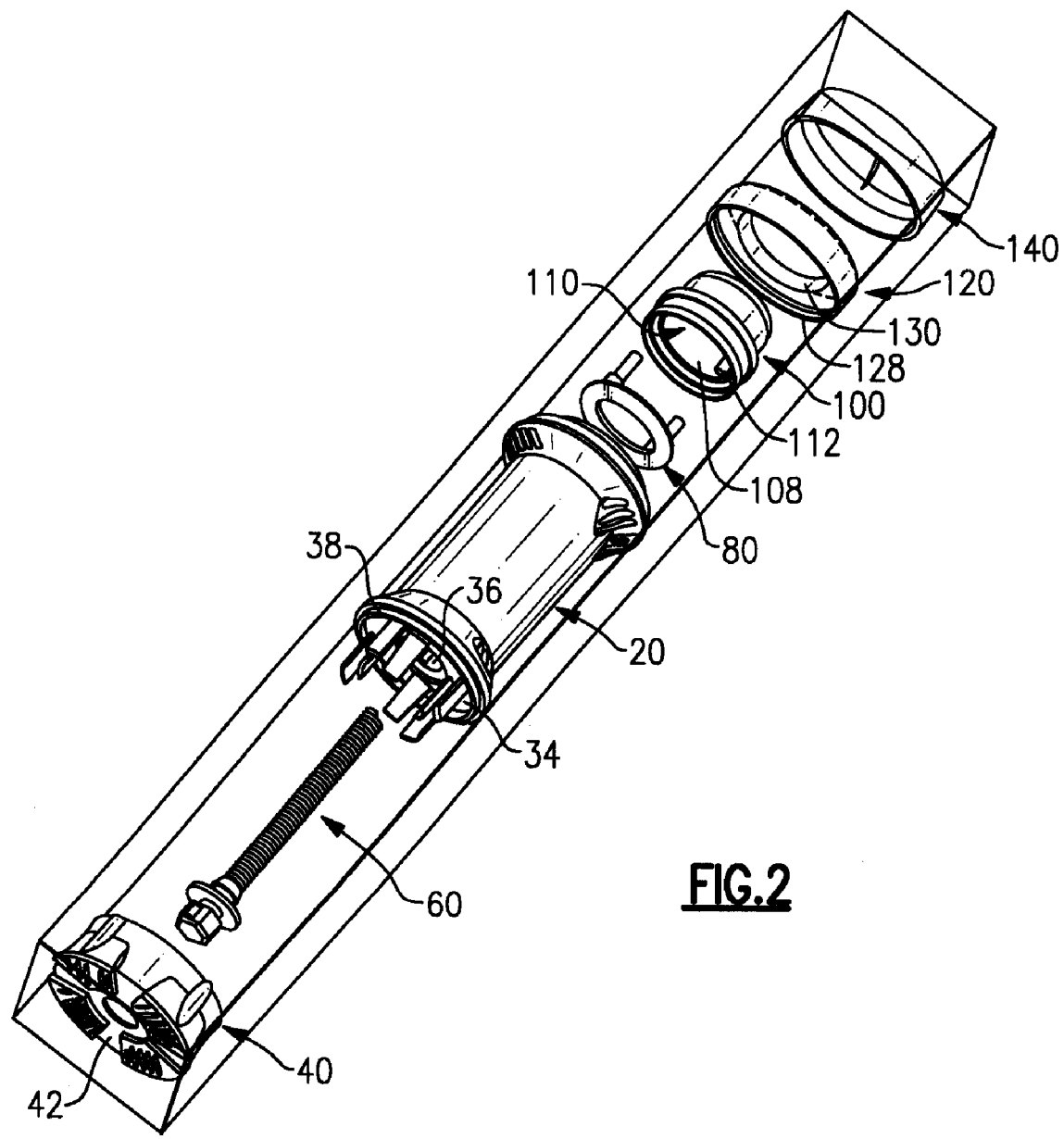
FIG. 2 is an exploded schematic view.
Figure 3:
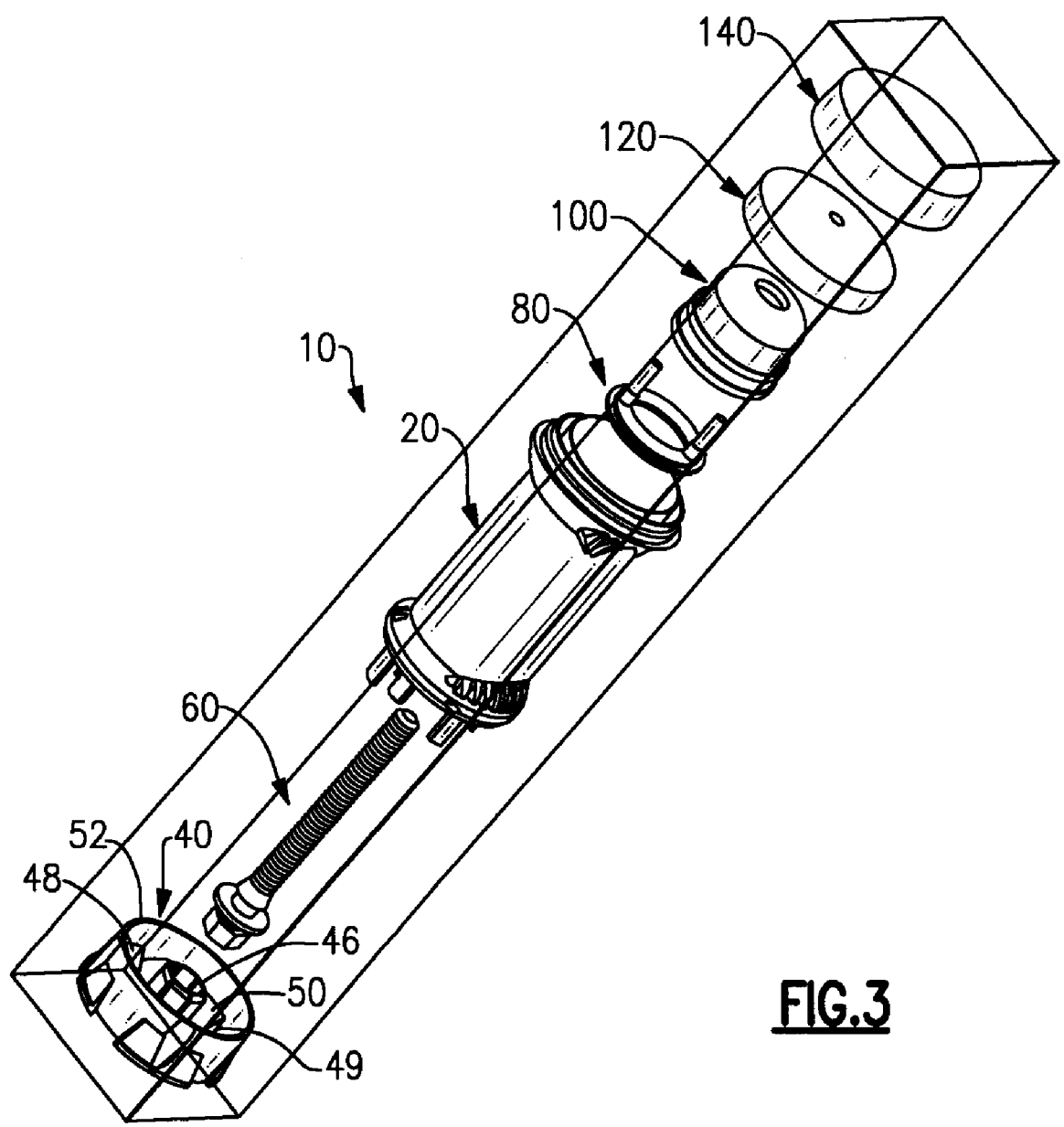
FIG. 3 is another exploded schematic view.
Figure 4:
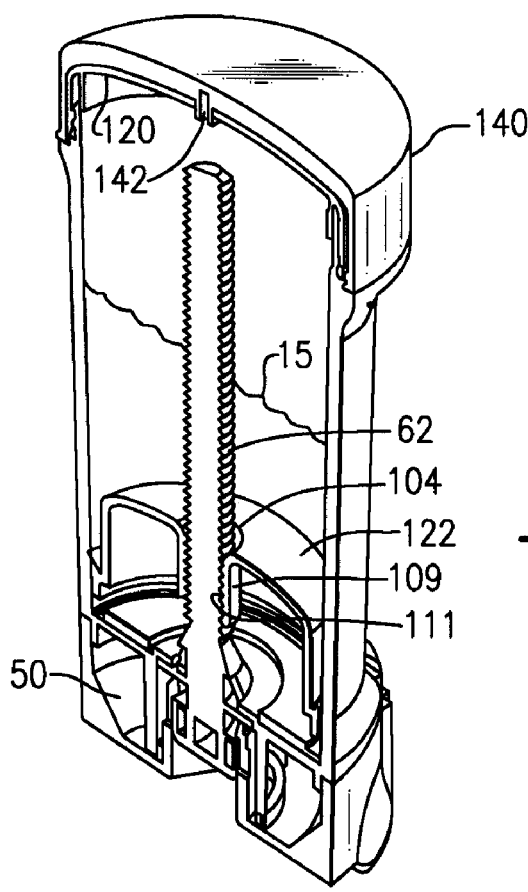
FIG. 4 is a partial cutaway view of an assembled dispenser.
Figure 5:
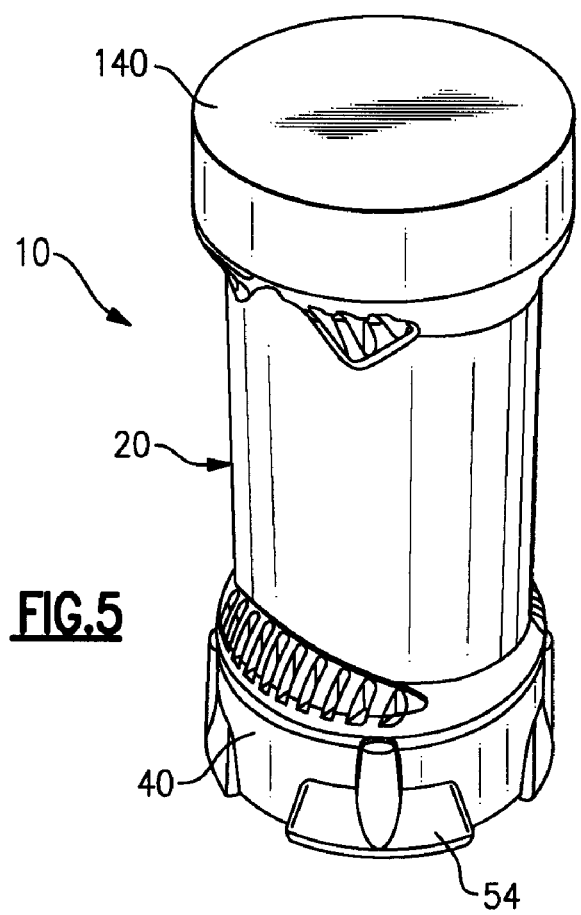
FIG. 5 is a perspective view of an assembled dispenser.
Figure 6:
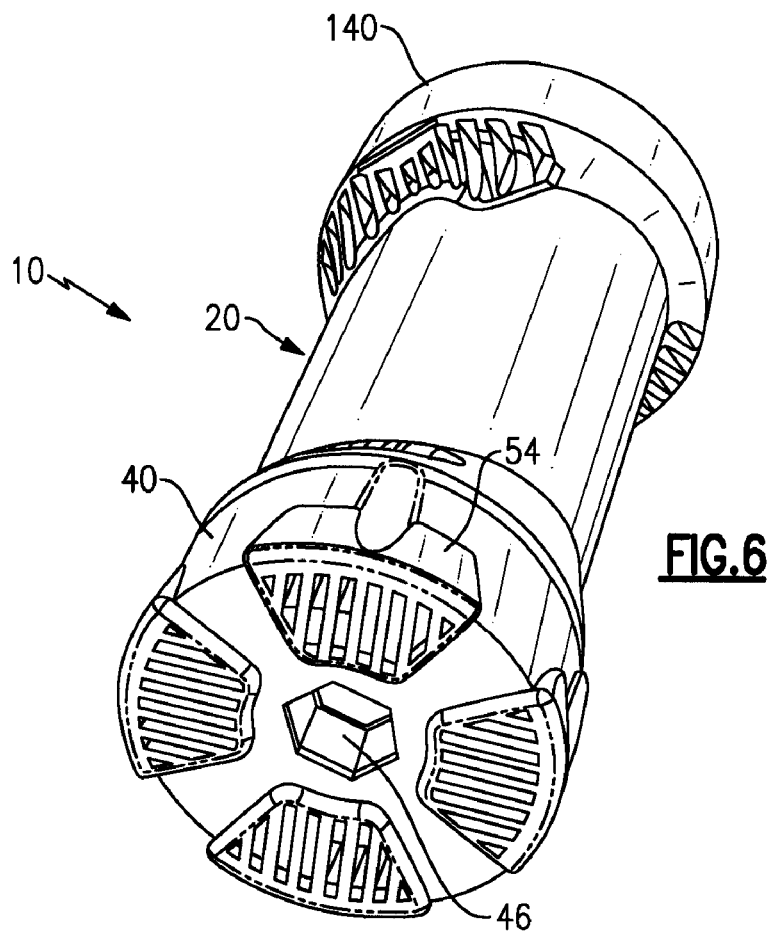
FIG. 6 is another perspective view of an assembled dispenser and showing the bottom area.

FIGS. 1-6 show one exemplary embodiment of a dosing dispenser 10 according to the present invention for dispensing a cream 15 or a gel or other flowable material. For the purposes of the present disclosure, the term cream will be used as a nonlimiting example of such a material. The dispenser 10 has the following main components: a body 20, a base 40, a drive screw 60, a ring 80, a riser 100 incorporating a fluid tight seal, an applicator pad 120 and a cap 140. Other than the fluid tight member 100 the parts may be made of polymer, plastic, composite or other formable or moldable material. The material preferably is plastic. The fluid tight member 100 is preferably made at least partially of a material having some degree of flexibility.

The body 20 comprises an outer wall 22, an inner wall 24, a first end 26 and a second end 28. The inner wall 24 defines a chamber 29 which can hold the cream 15. The first end 26 has an external rim 30. The second end 28 has a plurality of tabs 32 projecting downward from a plate 34. The tabs 32 are partially flexible. The plate 34 has a hole 36 extending therethrough. The body 20 may have a rim 38. The body 20 snap fits onto the base 40.

The base 40 comprises a bottom portion 42, sidewall 44, bush 46 and ratchet steps 48. The bush extends upward from the bottom portion 42. The ratchet steps 48 are attached to the inner sidewall 44 and have an angled portion 50. In one exemplary embodiment four ratchet steps 48 are used, but, it is to be understood that fewer or more may be used, depending on the design. The ratchet steps 48 are preferably curved and/or angled and also preferably have a gentle angled rise leading to a steep drop. The sidewall 44 may have a lip 52 which can mate with the rim 38 of the second end 28 of the body 20. The base may optionally include one or more feet 54 extending outward from the bottom portion 42 to assist in stabilizing the dispenser 10 when in a standing position and to facilitate gripping of the base 40 by a user.

The drive screw 60 comprises an elongated shaft 62 having a set of external threads 64, a first end 66 and a second end 68. The second end terminates in a cog 70 or a nut. The cog 70 preferably has a geometric cross-sectional shape, such as, but not limited to, square or hexagonal. The cog 70 can be inserted into the bush 46, which also preferably has a complementary geometric shape to accommodate the cog 70. Proximate to the second end 68 is a ring 72. An annular angled flange 74 is proximate to the ring 72. The shaft 62 can pass through the hole 36 in the body 20.

The ring 80 has a hole 82, a raised portion 84 forming a shoulder 86 and at least one, and preferably two pins 88, 90 extending upward from the raised portion 84. The pins 88, 90 may have a narrower diameter portion 92, 94. The hole 82 is preferably slightly smaller in diameter than the diameter of the ring 72.

The riser 100 has a preferably curved or domed top surface 102 having a hole 104 therein and also has a sidewall 106 which forms an inner wall 108 defining an interior space 110. Extending downward from the top surface 102 is a bush 109 having a set of internal threads 111. At least one, and preferably two sleeves 112, 114 are disposed in the interior space 110 and attached to the inner wall 108. The sleeves 112, 114 are sized to slidingly accommodate the pins 88, 90. An annular fluid tight member 116 is associated with the lower portion 118 of the riser 100. The fluid tight member 116 comprises a first annular sealing ring 118 and, preferably, a second annular sealing ring 119. Both first and second sealing rings 118, 119 are at least partially flexible and can form a fluid tight seal with the inner wall 24 of the body when the riser 100 is inserted in the chamber 29.

An applicator pad 120 has a preferably curved or domed top surface 122 having at least one hole 124 therein and a sidewall 126. The sidewall 126 preferably has an inner groove 128 which can be snapped over the external rim 30 on the body 20. Optionally, the applicator pad 120 may have a bush 130 extending downward from the top surface 122.

The cap 140 is sized to snugly fit over the applicator pad 120 to prevent contamination of the pad and to reduce evaporation of the cream 15.

To assemble the parts and charge the dispenser 10 with cream, the cog 70 is fitted into the bush 46 in the base 20. The ring 80 pins 88, 90 are inserted into the sleeves 112, 114 of the riser 100. The riser 100 and ring 80 are inserted into the first end 26 and down into the chamber 29. The shaft 62 is inserted into the hole 36 of the body and the ring 80 and riser 100 are slid over the shaft 62 until the ring 80 rests on the ring 72. The bush 109 is threaded using the threads 111 onto the threads 64 of the shaft 62. The chamber is filled with the appropriate measured amount of cream 15. The base 20 is turned so that the shaft 62 turns and advances the riser 100 and cream 15 toward the first end 26 of the body 20. The applicator pad 120 is snapped onto the top of body 20. The base 20 is turned and the riser 100 is advanced until there is essentially no air in the chamber 29 between the cream 15 and the applicator pad 120. The cap 140 is placed on the applicator pad 120 and the dispenser 10 is ready for use.

The user removes the cap 140 and turns the base 20 the appropriate amount of clicks (typically as directed on the instructions given to the user by the dispensing physician or pharmacy). As the base 20 is turned, the tabs 32 flex and move over the angled portions 50 of the ratchet steps 48. As the tabs 32 reach the vertical steps 49 the tabs 32 snap back vertical, thereby causing an audible click for each stop of the base. Also, the user may sense a vibration as the tabs 32 move over the ratchet steps 48. The vertical step 49 substantially prevents (or, at a minimum, makes it difficult to) reverse rotation of the base 20. With each click a predetermined amount of cream 15 is forced by the rising riser 100 to be dispensed through the holes 124. The dispensed cream 15 forms a bead or pool over the central area of the top surface 122 of the applicator pad 120. The user applies the cream 15 to the skin by rubbing the applicator pad 120 on the skin. The cream 15 at least partially spreads out over the surface 122 and is rubbed into the skin.

The tactile and audible click heard as the base 20 is turned provides feedback as to how much cream 15 is dispensed. For example, the prescription might be for 1 cc of cream per dose to be applied to the skin. If each click is 0.25 cc, for example, then the prescription might instruct the user to turn the base 20 to hear four clicks so as to dispense 1 cc of cream 15. The design of the present invention substantially prevents reverse rotation of the base 20 with respect to the body 40 so that cream 15 is not inadvertently sucked back into the dispenser, which may reduce the effective dosage dispensed and may contaminate the cream 15 in the chamber 29. The click also provides positive feedback when the right amount of cream 15 has been dispensed per turn.

Optionally, the cap 140 may have downward projecting protrusions 142 which are receivable within the holes 124. The protrusions 142 substantially seal the holes 124 when the cap 140 is in place, thereby reducing the risk of contamination of the cream 15 and preventing clogging of the holes 124. Preferably, the cap 140 has a registering means to align with the applicator pad 120 to make alignment of the protrusions 142 and the holes 124 easier.

Figure 7:
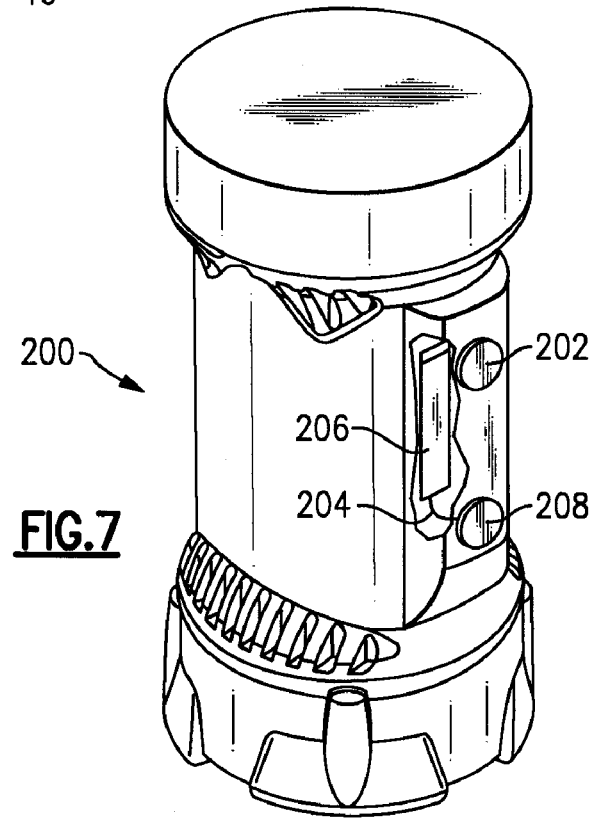
FIG. 7 is a schematic view in partial cutaway of a first alternative embodiment showing a vibration mechanism integrated with the dispenser.

The dispenser of the present invention may optionally also include a vibration mechanism whereby the dispenser 10 and, in particular, the applicator pad 120 area vibrates when activated so as to improve transfer of the cream 15 to the skin. In one exemplary embodiment, shown in FIG. 7, a dispenser 200, similar to the dispenser 10, also includes a battery 202, wiring 204, a vibrator mechanism 206, and a power switch 208. The vibrator mechanism 206 may be one of several possible mechanisms known to those skilled in the art.

The dispenser of the present invention may also include an indicator mechanism either to show the approximate number of remaining doses or to show when the chamber 29 is near empty, both so that the user can have advance awareness that a refill may be needed.

Figure 8:
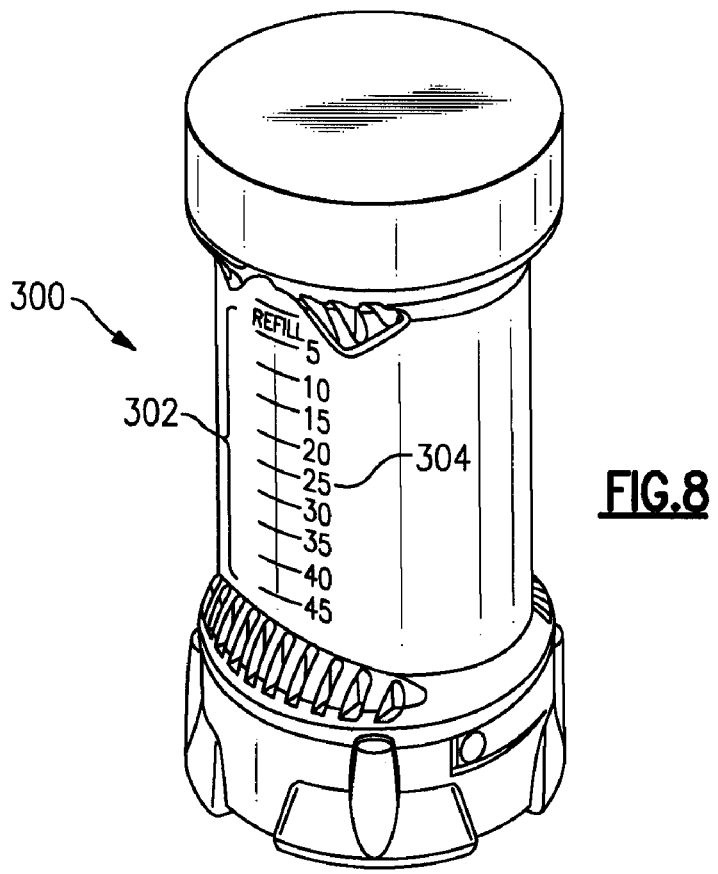
FIG. 8 is a perspective view of one alternative embodiment of a dispenser having measuring indicia on the side of the body.

In one exemplary embodiment of an indicator, shown in FIG. 8, a dispenser 300 may have a ruler 302 with set of marks 304 along the side of the body 20, with each mark being correlated to a particular quantity of cream 15 remaining in the dispenser 300. In this embodiment the body 20, or at least a portion thereof (such as an elongated window are extending from the first end 26 to near the second end 28) is preferably clear or translucent.

Figure 9:
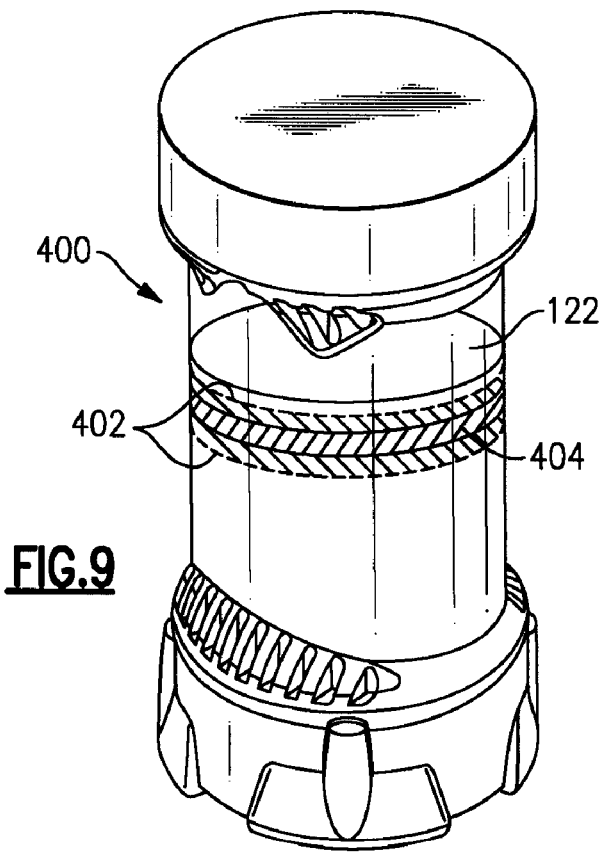
FIG. 9 is a perspective view of a second alternative embodiment of a dispenser having a colored ring on the body.

In a second exemplary embodiment of an indicator, shown in FIG. 9, a dispenser 400 the body 20 is at least in part clear or translucent and a colored ring 402 is disposed proximate to the first end 26 and the fluid tight member 116 has a colored ring 404 associated therewith. The rings 402 and 404 may be different colors. When the ring 404 moves up with the riser 10 toward the first end 26 it will eventually, after a certain number of dosings (i.e., turns of the base 20) overlap the ring 402. The overlap will combine the two colors to produce a third color. For example, if the ring 404 is yellow and the ring 402 is blue, the overlap color may be green, indicating time to go refill the dispenser.

Figure 10:
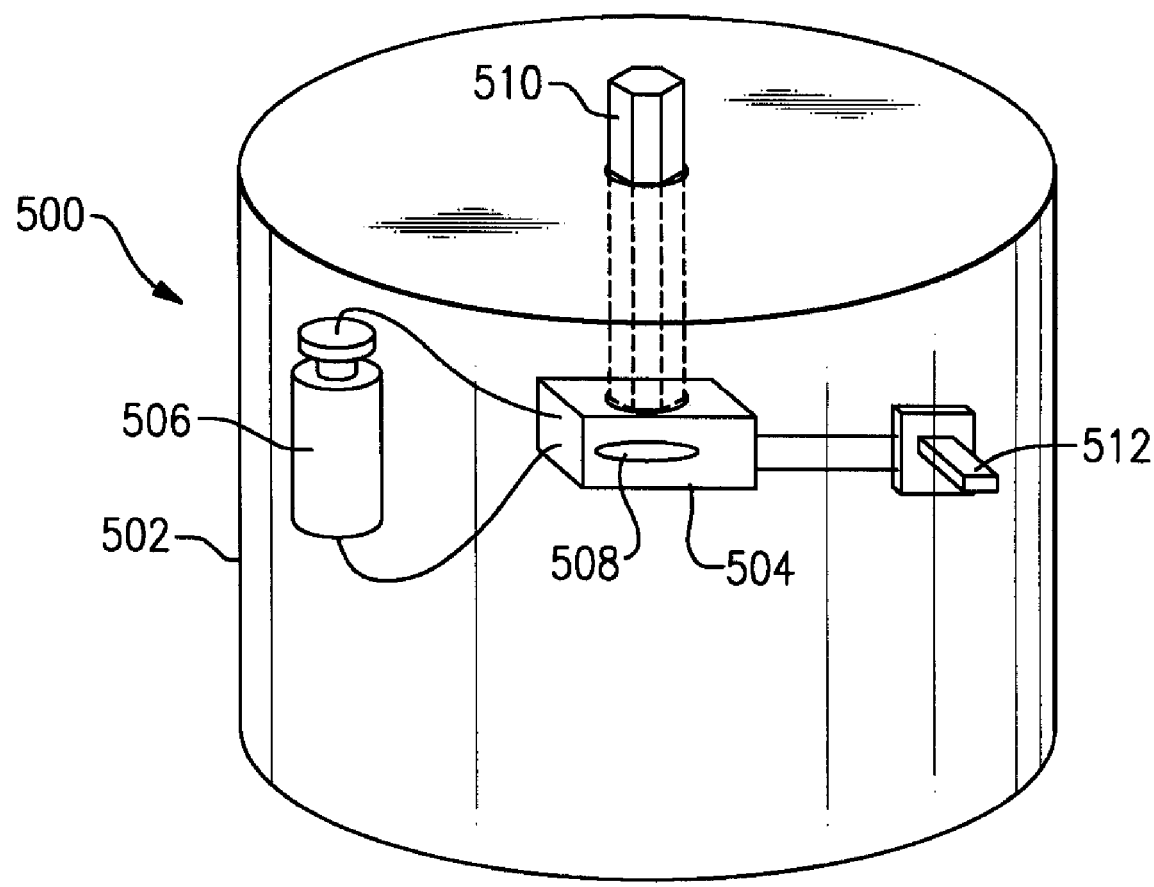
FIG. 10 shows a perspective view in cutaway of an exemplary embodiment of a loading mechanism with a vibratable base that can accommodate the dispenser.

The pharmacist must fill the dispenser by charging the chamber 29 with cream 15. The base 40 must be turned to advance the riser 100 toward the applicator pad 120 to eliminate the air gap. To eliminate bubbles and air pockets which may have formed during charging, it may be preferable to agitate the dispenser 10 so that the air rises out of the cream 15. In one exemplary embodiment the present invention also includes a separate loading unit. As shown in FIG. 10, a loading unit 500 comprises a base housing 502 which holds a motor 504, power source 506 (e.g., a battery, a wire to an AC outlet, or the like), a vibration mechanism 508 (e.g., motor and out-of-balance mechanism to induce vibration), a post 510, and a power switch 512. To use, the pharmacist or other qualified refiller places the dispenser 10 and base 40 on the post 510. Cream 15 is loaded into the chamber 29. The applicator pad 120 is placed on the first end 26 and threaded tight. The switch 512 is activated and the motor 504 turns the post 510, which in turn rotates the base 40 and the shaft 62, which causes the riser 100 to advance with the load of cream 15 toward the applicator pad 120. This is substantially faster and easier for the pharmacist than manually turning the base each time a dispenser needs to be charged. As the vibration mechanism 508 agitates the body 20 and the cream 15, air in the chamber and any pockets can be released. When done, the pharmacist deactivates the switch 512 and removes the dispenser 10 from the housing 502 and the post 510. Alternatively, rather than a switch 512, a pressure switch 513 (not shown) can be utilized so that the vibrator is activated when the user places the dispenser 10 on the post 510 and deactivated when the user removes the dispenser 10 from the post 510.

The present invention also contemplates the optional incorporation of a safety cap to prevent children from accessing the cream 15. In one exemplary embodiment of a safety cap, shown in FIGS. 11A-K, a dispenser 600 includes a safety cover 602 which fits over substantially the entire body 20. The bottom edge 604 of the cover 602 has an inward extending rim 606 or series of spaced apart rim portions which snap fits over a set of complementary protrusions 608 extending outward from the base 40. Each protrusion 608 has a notch 609 and a step portion 610. The top 611 of the cover 602 has a series of inwardly curved tabs 612 disposed within openings 614. In use the cover 602 is fitted over the dispenser 600 and the bottom rim 606 fits over the protrusions 608. The cover 608 is rotated clockwise and the rim 606 flexes into the notch 609 area over the step 610. The tabs 612 contact the cover 140 and urge the cover 602 upward, thereby biasing the rim portions 608 into the notches 609 and locking the cover 602 onto the dispenser 600. When the user desires to use the dispenser 600, he or she grasps the base 40 in one hand and the cover 602 in the other and presses downward on the cover 602 (as shown by arrow 620 and rotates the cover 602 counterclockwise, thereby disengaging the rim portions 608 from the notches 609.

In a second embodiment of a safety cap, shown in FIGS. 12A-D, a dispenser 700 includes a preferably horizontal finger 702 extending from the base 40 in a coplanar manner. The finger 702 has the ability to flex slightly. The finger 702 includes a button 704. When the button 704 is depressed the finger 702 flexes and allows the base 40 to turn with respect to the body 20.

The following are alternative embodiments of various dispenser designs.

Figure 13A:
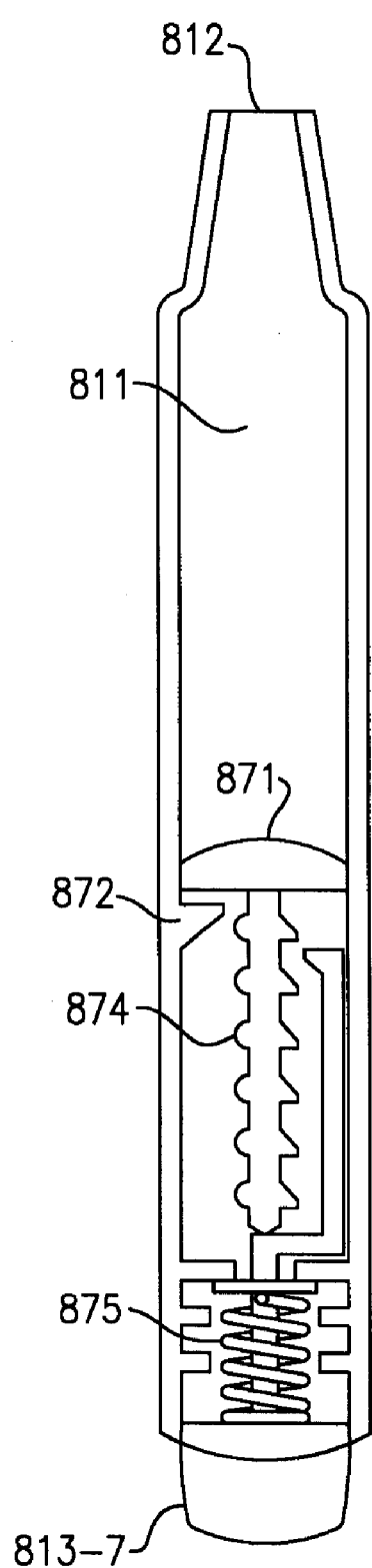
FIGS. 13A and 13B show an alternative embodiment of a "pen click" design of a dispenser.
Figure 13B:
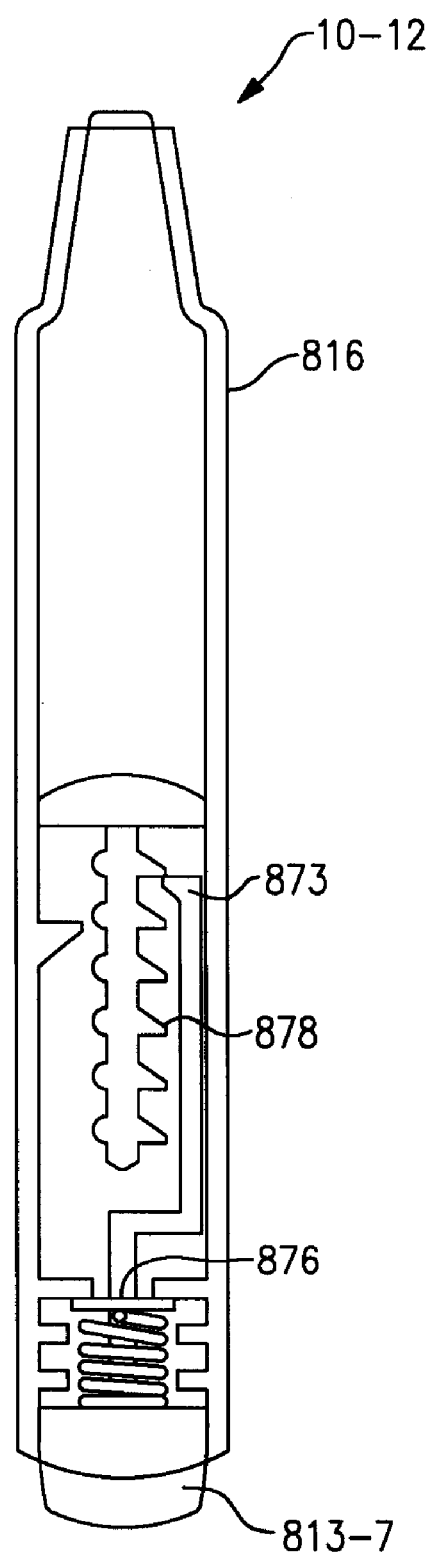

FIGS. 13A-B depict an exemplary embodiment of a dispensing system 810-12 comprising a button 813-7 which is pressed to dispense a cream 15. The dispensing system 810-12 comprises a case 816, a medicine output interface 812, a button 813-7, and a plunger 871. The case 816 comprises a tab 872. The button 813-7 comprises a handle 873, a spring 875, a piston 873, and a piston guide 876. The plunger 871 comprises click tabs 874 and support grooves 878. The dispensing mechanism comprises a user pressing the button 813-7 which in turn compresses the spring 875. The spring 875 applies pressure regulated by the piston guide 876 to the piston 873. The piston 873 moves the plunger 871 by applying pressure to the support groove 878. The click tab 874 on the plunger 871 makes contact with the tab 872 producing an audible click. The spring 875 returns the piston 873 to the start position after moving the plunger 871 up one notch on the support grooves 878.

Figure 14B:
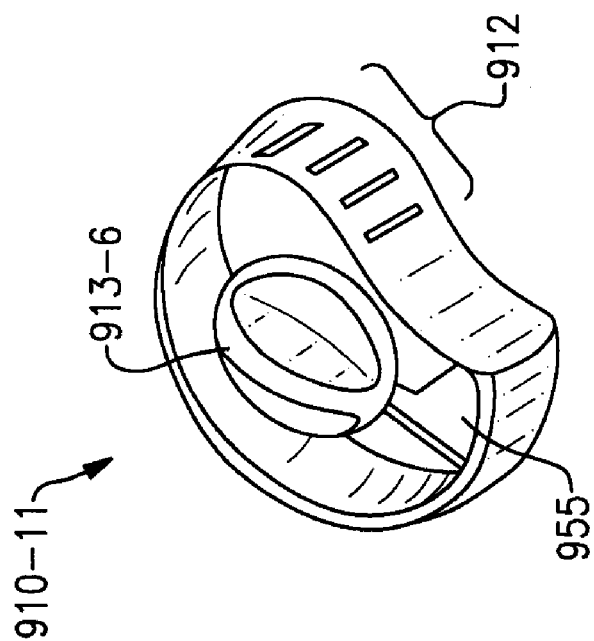
FIGS. 14A and 14B show an alternative embodiment of a round design of a dispenser.
Figure 14A:
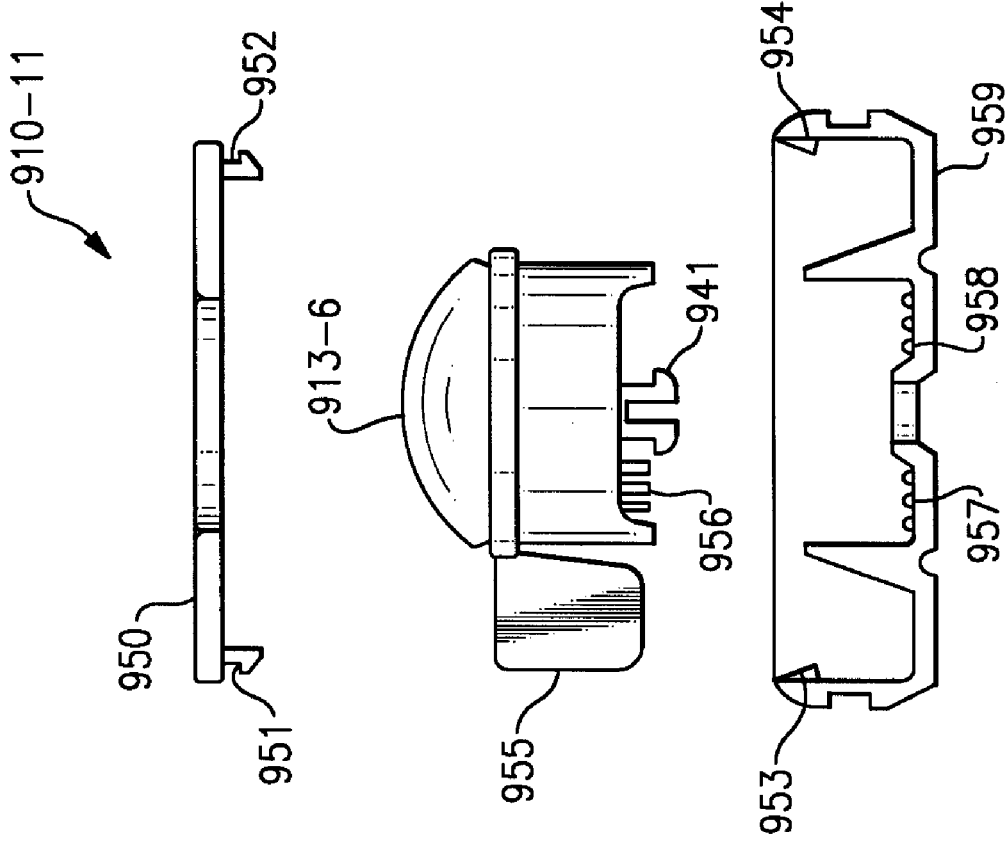

FIGS. 14A-B depict a cross-sectional view of a dispensing system 910-11 comprising a user input dial 913-6 which is turned to dispense medicine. The cross-section of the dispensing system 190-11 comprises a cover 950, a user input dial 913-6, and a base 959. The cover 950 comprises a tab 951 and a tab 952 which attaches to a groove 953 and a groove 954 on the base 959 to connect the cover 950 to the base 959. The user input dial 913-6 comprises a paddle 955, a screw 941, and a tab 956. The paddle 955 rotates with the user input dial 913-6 pushing medicine to the medicine output interface 912. The screw 941 connects the input knob to the base 959. The tab 956 makes contact with a groove 957 and a groove 958 on the base 959 to produce an audible click as the user input dial 913-6 is rotated. This audible click notifies the user of the dosage.

FIG. 14B depicts an internal view of a dispensing system 910-11 comprising a user input dial 913-6 which is turned to dispense medicine. The dispensing system 910-11 comprises a paddle 955, a user input dial 913-6, and a medicine output interface 912. The paddle 955 moves responsive to turning the user input dial 913-6. Medicine is dispensed to the medicine output interface 912 by the movement of the paddle 955.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

It should further be noted that any patents, applications and publications referred to herein are incorporated by reference in their entirety.

What is claimed is:

1. A dispenser for providing measured amounts of a fluid or semi-fluid of cream or gel and having a safety cover, the dispenser comprising:
 a) a body comprising
  i) a first end having external threads,
  ii) a second end,
  iii) an inner wall and an outer wall,
  iv) a chamber defined by said inner wall,
  v) said second end having a plurality of downward projecting tabs;
 b) a base comprising
  i) a bottom portion,
  ii) a side wall including a locking means for removably securing said body,
  iii) an interior area,
  iv) a bush extending axially upward from said bottom portion,
  v) a plurality of angled ratchet steps;
 c) a drive screw comprising
  i) male threads thereon,
  ii) a first end,
  iii) a second end terminating in a cog, said cog being receivable within said base bush,
  iv) an annular flange portion proximate to said second end,
  v) a ring extending annularly outward from and proximate to said second end and disposed between said cog and a ring attached to a riser;
 d) said ring attached to said riser further comprising
  i) an annular disk having a hole therein, said hole being smaller than the diameter of the drive screw ring,
  ii) a positioning means comprising a plurality of pins extending axially upward from said disk surface, each said pin having a shoulder forming a portion having a larger diameter than the remaining portion of said pin;
 e) said riser further comprising
  i) an upper portion having a rounded top surface and a hole defined therein,
  ii) an inner wall,
  iii) an outer wall,
  iv) a bush extending downward from said top surface inside said upper portion, said bush and said hole defining a secondary orifice and said bush having a set of internal threads capable of mating with said drive screw threads,
  v) a lower portion including
   a) a first sealing ring portion made of an at least partially flexible material,
   b) a second sealing ring portion made of an at least partially flexible material,
  vi) a plurality of sleeves mounted axially on said inner wall of said fluid tight member,
  vii) said fluid tight member receivable within said body chamber such that said first and second sealing ring portions form substantially fluid tight seals with said body inner wall when disposed therein;
 f) an applicator pad comprising
  i) at least one hole therein,
  ii) a sidewall having an internal annular groove which can snap onto said second end of said body,
  iii) a bush;
 g) a cap fittable over said applicator pad; and
 h) a safety cap comprising
  i) a generally cylindrical cover,
  ii) a top associated with said cover,
  iii) a plurality of openings in said top,
  iv) a plurality of flexible tabs, one tab associated with each said opening in said top, said tabs capable of contacting said cap cover and biasing said safety cap upward,
  v) a bottom edge having an inwardly extending rim, and
  vi) a plurality of protrusions extending outward from said base and over which said inwardly extending rim may be fitted, each said protrusion having a notch and a step portion for engaging said inwardly extending rim.

* * * * *